US006454734B1

(12) United States Patent
Deacon

(10) Patent No.: US 6,454,734 B1
(45) Date of Patent: Sep. 24, 2002

(54) APPARATUS FOR CONTROLLING THE AMOUNT OF TENSION DISTRIBUTED TO A PATIENT BY A TRACTION MEANS

(76) Inventor: William John Deacon, 10 USA St., Brampton, Ontario (CA), L6T 4N4

(*) Notice: Subject to any disclaimer, the term of this patent is extended or adjusted under 35 U.S.C. 154(b) by 72 days.

(21) Appl. No.: 09/660,643

(22) Filed: Sep. 13, 2000

(51) Int. Cl.[7] .................................................... A61F 5/00

(52) U.S. Cl. ............................ 602/32; 606/241; 602/36

(58) Field of Search ............................... 602/32–36, 38; 606/237–241

(56) References Cited

U.S. PATENT DOCUMENTS 4,033,339 A * 7/1977 Roberts ....................... 602/18
5,115,802 A * 5/1992 Dyer ........................... 602/33
5,830,162 A * 11/1998 Giovannetti ................. 601/23
5,865,781 A * 2/1999 Lieber ......................... 602/32

* cited by examiner

*Primary Examiner*—Denise M. Pothier
(74) *Attorney, Agent, or Firm*—Bachman & LaPointe, P.C.

(57) ABSTRACT

An apparatus for controlling the amount of tension distributed to a patient receiving traction including a gripping structure having a switching sensor to sense action commands from the patient, a control consul communicated with the switching sensor so as to receive action commands from the switching sensor and process the action commands so as to create processed commands, and a traction device for applying tension to the patient, the traction device includes a tensioning device communicated with the control consul so as to receive processed commands from the control consul, wherein the tensioning device controls the traction device so as to engage or disengage the traction device.

14 Claims, 1 Drawing Sheet

APPARATUS FOR CONTROLLING THE AMOUNT OF TENSION DISTRIBUTED TO A PATIENT BY A TRACTION MEANS

BACKGROUND OF THE INVENTION

The present invention is directed to an apparatus for controlling the amount of tension distributed to a patient undergoing a medical traction procedure.

Conventional means of controlling the amount of tension distributed from a traction table to a patient during traction procedures are inadequate and fail to prevent a patient from experiencing injury and discomfort by allowing too much tension to be distributed. One reason for this failure to limit the tension distribution is that earlier designs provide for an outside party, such as a doctor or a medical technician, to release the tension being applied to a patient upon patient request, causing the patient to be in pain before the tension is decreased or removed. In addition, patients tend to experience more stress when they are not in control of their treatment. This tendency prevents the patient from relaxing and causes the patient to 'fight' the traction which causes the patient injury.

A need remains for a device that will allow a patient to control the amount of tension distributed during a medical traction procedure thereby allowing the patient to receive the amount of traction tension needed without causing the patient undue pain, yet allowing the patient to decrease traction tension upon discomfort thereby preventing injury.

Heretofore, a variety of devices have been utilized in connection with distributing and controlling tension to patients on traction tables. Examples of these prior devices are disclosed in U.S. Pat. Nos. 4,995,378 to Dyer and 1,950,948 (expired).

SUMMARY OF THE INVENTION

In accordance with the present invention, the foregoing objects and advantages are readily attained.

According to the present invention, an apparatus for controlling the amount of tension distributed to a patient receiving traction is provided which comprises a gripping structure having a switching sensor to sense action commands from a patient, a control consul communicated with the switching sensor so as to receive action commands from the switching sensor. The action commands are then processed so as to create processed commands. The apparatus includes a traction device for applying tension to the patient wherein the traction device includes a tensioning device, having a tension sensing device, communicated with the control consul so as to receive processed commands from the control consul, wherein the tensioning device controls the traction device so as to engage or disengage the traction device.

It is an objective of the present invention to provide an apparatus for controlling, and more particularly for allowing the patient to control, the amount of tension distributed to a patient by a traction table while allowing the patient to receive the needed amount of tension.

Other objects and advantages will appear hereinbelow.

BRIEF DESCRIPTION OF THE DRAWINGS

A detailed description of preferred embodiments of the present invention follows, with reference to the attached drawings, wherein like numerals depict like elements.

DETAILED DESCRIPTION

Figure 1:
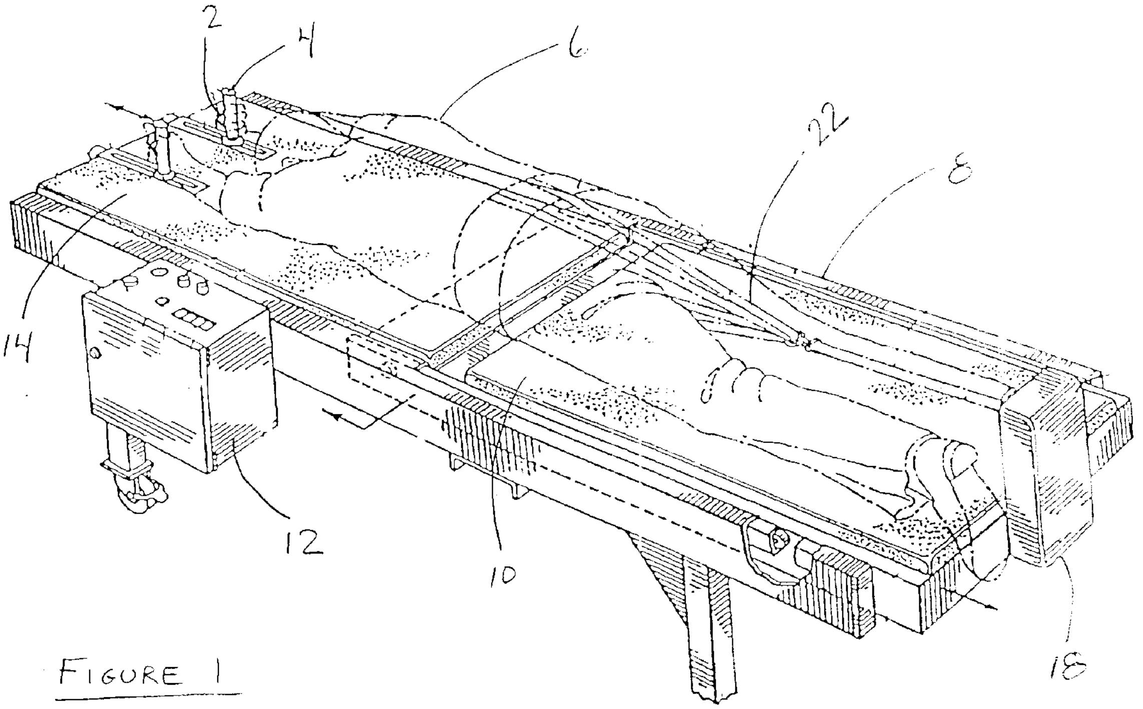
FIG. 1 illustrates a patient undergoing a medical traction procedure using a traction device showing the method of the present invention.

This invention relates to an apparatus for controlling the amount of traction tension distributed to a patient by a traction tension producing means wherein the tension distribution is switch controlled by the patient and wherein the tension producing device is capable of disengagement upon switch activation.

In accordance with the present invention, an apparatus for controlling the amount of tension distributed to a patient by a traction device is provided which preferably has a gripping structure having a switching sensor to sense action commands from a patient, a control consul communicated with the switching sensor, wherein the control consul includes a microprocessor and a Programmable Logic Controller (PLC) for processing action commands received from the switching sensor thus creating processed commands, and a traction device for supporting and applying tension to a patient wherein the traction device includes a tensioning device which is communicated with the control consul for receiving and carrying out processed action commands. This allows the tensioning device to control the engagement or disengagement of the traction device, thereby controlling the amount of tension, the rate of tension increase being applied and the rate of tension decrease being removed from the patient. In addition, in accordance with the present invention the control consul preferably provides an input device for entering a predetermined tension limit to be applied to the patient so as to prevent the traction device from exceeding desired tension levels. Also, the control consul is communicated with the switching sensor so as to receive action commands from the switching sensor.

In accordance with the present invention, the switching sensor is preferably patient activated and controlled and may be a simple mechanical switch, a pressure switch or an electrical switch controlled by pressure, proximity (either inductive or capacitive), photoelectric or temperature or the like. In addition, the switching sensor is preferably of any type suitable to the desired end product. In accordance with the present invention, the traction device is preferably a supporting structure capable of supporting a patient while the patient is receiving traction. The traction device preferably comprises a supporting structure for supporting a patient and a traction structure for applying tension to a patient, wherein the traction structure is movably associated with the supporting structure. In addition, the traction device includes a harness or the like, for attaching the patient to the traction structure so as to anchor the patient to the traction structure and the traction device is capable of operating in a plurality of modes, these modes being application mode, maintenance mode and retraction mode. When the traction device is operating in application mode, the traction device is engaged and the tensioning device is moving the traction structure relative to the supporting structure so as to separate the supporting structure from the traction structure. When the traction device is operating in retraction mode, the traction device is disengaged and the tensioning device is moving the traction structure relative to the supporting structure so as to bring the traction structure and the supporting structure close together. When the traction device is operating in maintenance mode, the tensioning device is acting to maintain the position of the traction structure so as to keep the traction structure stationary relative to the supporting structure.

In accordance with the present invention, the gripping structure comprises a switching sensor and is preferably adjustable in size and position, so as to allow for usage by patients of various sizes. As long as the patient is able to access the gripping structure, it is considered within the scope of the invention that the gripping structure can be located anywhere within the vicinity of the traction device and does not necessarily have to be attached to the traction device. It should be noted that a patient activatable switch is meant to refer to a switch that can be operated by a patient while the patient is anchored to the traction device. The control consul preferably comprises a means for entering a desire tension limit and rate at which tension is to be applied to and removed from the patient. In addition, the traction device comprises a tension sensing device to measure and monitor the amount of tension being applied to the patient. This tension sensing device is communicated with the control consul so as to communicate tension related data (level and rate of application, etc) to the control consul. The action commands, tension limit and rate and the measured tension values are communicated to the control consul for input into a microprocessor and a PLC located within the control consul for processing these values so as obtain processed commands. The control consul communicates the processed commands to the tensioning device, which will control the tensioning device and hence the amount of tension being applied to the patient.

Figure 2:
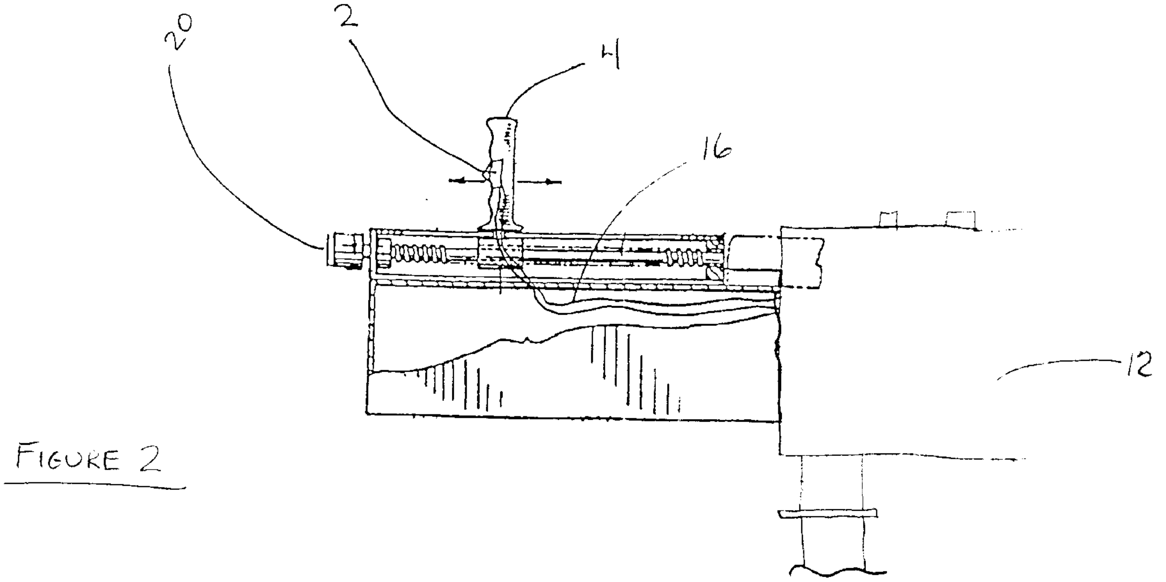
FIG. 2 illustrates a gripping structure showing a switching sensor in accordance with the present invention.

Referring to the drawings, FIGS. 1 AND 2 illustrate an apparatus for controlling the amount of tension distributed to a patient receiving traction in accordance with the present invention and preferably includes patient 6 engaging gripping structure 4 having switching sensor 2 communicated with control consul 12, wherein gripping structure 4 is movably disposed on a traction device 8 having supporting structure 14 and traction structure 10. Also, in accordance with the present invention, control consul 12 is communicated with tensioning device 18 so as to engage traction device 8. Gripping structures 4 are adjusted to suit the height and length of patient 6 by adjusting adjustment device 20. In one embodiment, a desired traction tension limit and application rate is entered into control consul 12 by patient 6 or a second party. These values are communicated with a microprocessor (not shown) and a PLC (not shown) located within control consul 12. Patient 6 then disposes himself on traction device 8 and secures himself to traction structure 10 using harness 22. Patient 6 holds gripping structure 4 engaging switching sensor 2 generating action commands. Switching sensor 2 communicates action commands to control consul 12 which processes these action commands and communicates the processed commands to tensioning device 18 which causes traction device 8 to switch into application mode thereby producing tension on harness 22 and hence producing tension on patient 6. A tension sensing device (not shown) located within tensioning device 18 is also communicated with control consul 12 and measures and monitors the amount of tension being distributed to patient 6 and communicates these values to control consul 12 for consideration in processing the action commands. In accordance with the present invention, as traction tension is being applied the tension sensing device (not shown) monitors tension being distributed to patient 6 and tensioning device 18 adjusts the tension level to conform to the entered limits. Once the traction tension level reaches the desired level, the traction device 8 switches into maintenance mode and maintains the current position of traction structure 10 in relation to the supporting structure 14. If the tension applied to patient 6 exceeds desired levels or if patient 6 desires to relieve the tension applied to harness 22 by traction device 8, patient 6 releases his grip on gripping structure 4 thereby engaging switching sensor 2 and switching traction device 8 into retraction mode. In accordance with the present invention, switching sensor 2 communicates action commands to control consul 12 which processes action commands and communicates processed command to tensioning device 18 causing traction device 8 to switch immediately into retraction mode thereby causing supporting structure 14 and traction structure 10 to move closer together. This decreases tension on harness 22 and hence decreases tension on patient 6. Because control consul 18 advantageously causes traction device 8 to switch immediately into retraction mode, injury to the patient is avoided and discomfort is minimize.

In addition, because patient 6 is in control of traction device 8, patient 6 experiences less stress and is allowed to relax. This reduces patient tendency to fight the traction tension. This reduction in the tendency to fight traction advantageously reduces the probability of further injury to patient 6.

It is considered within the scope of this invention, that gripping structure 4 may be located anywhere within reach of patient 6 and is not required to be attached to traction device 8. Also, it is considered within the scope of this invention, that supporting structure 14 may be movable relative to traction structure 10.

In accordance with the present invention, the apparatus for controlling the amount of tension distributed to a patient receiving traction and its components may be constructed of any material suitable to the desired end product.

Also, in accordance with the present invention, the apparatus for controlling the amount of tension distributed to a patient receiving traction advantageously provides a device that allows patient 6 to control his therapy thereby preventing further injury to patient 6.

It is to be understood that this invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

I claim:

1. An apparatus for controlling the amount of tension distributed to a patient receiving traction comprising:

a gripping structure having a switching sensor sensing action commands from the patient;

a control consul communicated with said switching sensor so as to receive said action commands from said switching sensor and process said action commands creating processed commands; and a traction device for applying tension to the patient, said traction device includes a table supporting structure sized and configured to support the arms, torso and legs of the patient a tensioning device communicated with said control consul so as to receive said processed commands from said control consul, wherein said tensioning device controls said traction device so as to engage or disengage said traction device, and wherein said gripping structure is movably disposed on said traction device wherein the amount of tension distributed to the patient is controlled by releasing or engaging said switching sensor.

2. An apparatus according to claim 1, wherein said traction device comprises a supporting structure for supporting the patient and a traction structure for applying tension to the patient, said traction structure being movably associated with said supporting structure.

3. An apparatus according to claim 2, wherein said tract ion device includes a harness for attaching the patient to said traction structure so as to anchor the patient to said traction structure.

4. An apparatus according to claim 2, wherein said traction device comprises an application mode, a maintenance mode and a retraction mode, wherein when said traction device is in said maintenance mode, said traction structure is stationary relative to said supporting structure.

5. An apparatus according to claim 4, wherein when said traction device is in said application mode, said traction device is engaged and said traction structure is moving relative to said supporting structure so as to cause said traction structure and said supporting structure to separate.

6. An apparatus according to claim 4, wherein when said traction device is in said retraction mode, said traction device is disengaged and said structure is moving relative to said supporting structure so as to cause said traction structure and said supporting structure to unite.

7. An apparatus according to claim 1, wherein said gripping structure is movably attached to said traction device, said gripping structure being adjustable so as to accommodate patients of various sizes.

8. An apparatus according to claim 1, wherein said switching sensor is patient activatable and is a sensor selected from the group consisting of a simple mechanical switch, a pressure switch and an electrical switch.

9. An apparatus according to claim 8, wherein said electrical switch is selected from the group consisting of pressure, proximity, photoelectric and temperature actuated switches.

10. An apparatus according to claim 1, wherein said control consul includes a microprocessor and a Programmable Logic Controller (PLC) for processing measured data and said action commands.

11. An apparatus according to claim 1, wherein said traction device further comprises a tension sensing device for measuring and monitoring the amount of tension being applied to the patient, said tension sensing device being communicated with said control consul so as to communicate measured data to said control consul.

12. An apparatus according to claim 1, wherein said tensioning device controls the rate of tension increase being applied to the patient and the rate of tension decrease being removed from the patient.

13. An apparatus according to claim 1, wherein said tensioning device comprises a means for entering a tension limit to be applied to the patient, said tensioning device further acting to control the amount of tension applied to the patient, so as to conform to said tension limit.

14. An apparatus according to claim 1, wherein when said tensioning device receives said processed commands, said tensioning device acts to engage or disengage said traction device.

* * * * *